United States Patent [19]

Buchecker et al.

[11] Patent Number: 5,174,921
[45] Date of Patent: Dec. 29, 1992

[54] BICYCLOHEXYL-DERIVATIVES

[75] Inventors: Richard Buchecker, Zurich; Alfred Germann, Basel; Martin Schadt, Seltisberg; Alois Villiger, Basel, all of Switzerland

[73] Assignee: Hoffmann-La Roche Inc., Nutley, N.J.

[21] Appl. No.: 701,728

[22] Filed: May 20, 1991

[30] Foreign Application Priority Data

May 21, 1990 [CH] Switzerland ............... 1718/90

[51] Int. Cl.⁵ ............... C09K 19/30; C07C 19/08
[52] U.S. Cl. ............... 252/299.63; 570/129; 252/299.61
[58] Field of Search ............... 252/299.63; 570/129

[56] References Cited

U.S. PATENT DOCUMENTS

| | | | |
|---|---|---|---|
| 4,405,488 | 9/1983 | Sugimori et al. | 252/299.63 |
| 4,621,901 | 11/1986 | Petrzilka et al. | 350/350 R |
| 4,629,581 | 12/1986 | Petrzilka et al. | 252/299.63 |
| 4,676,604 | 6/1987 | Petrzilka et al. | 350/350 R |
| 4,724,097 | 2/1988 | Romer et al. | 252/299.63 |
| 4,886,621 | 12/1989 | Sage et al. | 252/299.61 |
| 5,013,477 | 5/1991 | Buckecker et al. | 252/299.63 |

FOREIGN PATENT DOCUMENTS

| | | |
|---|---|---|
| 315014 | 5/1989 | European Pat. Off. |
| 4025550 | of 0000 | Fed. Rep. of Germany |
| 3631611 | 4/1988 | Fed. Rep. of Germany |
| WO85/4874 | 11/1985 | World Int. Prop. O. |
| 8603769 | 7/1986 | World Int. Prop. O. |

OTHER PUBLICATIONS

Schadt, Program of "The 8th Liquid Crystal Conference of Socialistic Countries" Slides, Abstracts, Krakow, Poland, Aug. 28–Sep. 1, 1989.

Abstract of Dr. Schadt's presentation at "The 8th Liquid Crystal Conference of Socialistic Countries", Karkow, Poland, Aug. 28–Sep. 1, 1989.

*Primary Examiner*—Robert L. Stoll
*Assistant Examiner*—C. Harris
*Attorney, Agent, or Firm*—George M. Gould; George W. Johnston; William Krovatin

[57] ABSTRACT

Compounds of the formula

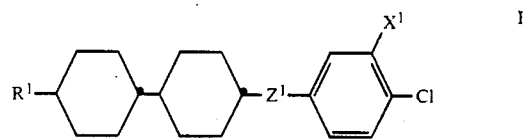

wherein $Z^1$ is a single covalent bond or $-CH_2CH_2-$, $X^1$ is hydrogen, fluorine or chlorine and $R^1$ is 1E-alkenyl with 2 to 12 carbon atoms, their preparation, liquid crystalline mixtures which contain these compounds and their use for electro-optical purposes.

10 Claims, No Drawings

BICYCLOHEXYL DERIVATIVES

BACKGROUND OF THE INVENTION

1. Field of the Invention

The present invention is concerned with novel bicyclohexyl derivatives, their preparation, liquid crystalline mixtures which contain these compounds and their use for electro-optical purposes.

2. General Discussion

Liquid crystals are used primarily as dielectrics in indicating devices, since the optical properties of such substances can be influenced by an applied voltage. Electro-optical devices based on liquid crystals are well-known to the person skilled in the art and can be based on various effects. Examples of such devices are cells having dynamic scattering, DAP cells (deformation of aligned phases), guest/host cells, TN cells having a twisted nematic structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields electromagnetic radiation. Further, the liquid crystals materials should have a low viscosity and in the cells should give short response times, a low threshold potential and a high contrast. Furthermore, at usual operating temperatures of about $-30°$ C. to about $+80°$ C., especially from about $-20°$ C. to about $+60°$ C., they should have a suitable mesophase, for example, a nematic or cholesteric mesophase for the cells referred to above. Further properties such as the electrical conductivity, the dielectric anisotropy and the optical anisotropy must fulfill different requirement depending on the type of cell and field of application. For example, materials for cells having a twisted nematic structure should have a positive dielectric anisotrpoy and an electrical conductivity which is as low as possible. For some years there has been a particular interest in actively addressed liquid crystal indicators, for example, TFT applications ("thin film transistor") in television sets. The use of cyano compounds having positive dielectric anisotropy leads, however, in such indicators mainly to an undesirably high increase in current.

Since liquid crystals are generally used as mixtures of several components, it is important that the components have a good miscibility with one another.

SUMMARY OF THE INVENTION

The present invention provides compounds of the formula

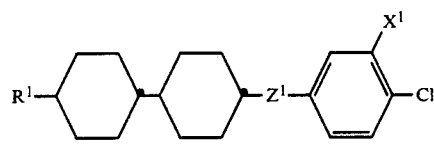

wherein $Z^1$ represents a single covalent bond or $-CH_2CH_2-$, $X^1$ denotes hydrogen, fluorine or chlorine and $R^1$ signifies 1E-alkenyl with 2 to 12 carbon atoms.

The compounds in accordance with the invention are liquid crystals having broad nematic phases and surprisingly high clearing points. At the same time, they surprisingly have short switching times, especially in indicating devices having a twisted nematic structure. They have a low viscosity, a good miscibility with usual liquid crystal materials and make possible comparatively low threshold potentials.

The compounds in accordance with the invention are especially suitable as components of nematic and cholesteric mixtures and, by virtue of their good miscibility with one another and with known liquid crystals materials, can be used in comparatively high concentrations.

DETAILED DESCRIPTION OF THE INVENTION

The invention concerns compounds of the formula

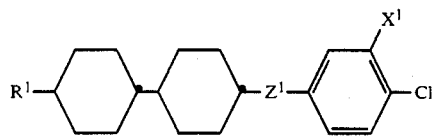

wherein $Z^1$ is a single covalent bond or $-CH_2CH_2-$, $X^1$ is hydrogen, fluorine or chlorine, and $R^1$ is 1E-alkenyl with 2 to 12 carbon atoms.

The compounds in accordance with the invention are liquid crystals having broad nematic phases and surprisingly high clearing points. At the same time, they surprisingly have short switching times, especially in indicating devices having a twisted nematic structure. They have a low viscosity, a good miscibility with usual liquid crystal materials and make possible comparatively low threshold potentials.

The compounds in accordance with the invention are especially suitable as components of nematic and cholesteric mixtures and, by virtue of their good miscibility with one another and with known liquid crystal materials, can be used in comparatively high concentrations.

The term "1E-alkenyl" above embraces straight-chain or branched residues. The straight-chain residues such as vinyl, 1E-propenyl, 1E-butenyl, 1E-pentenyl, 1E-hexenyl, 1E-heptenyl and the like are generally preferred.

Formula I embraces the compounds of the formula

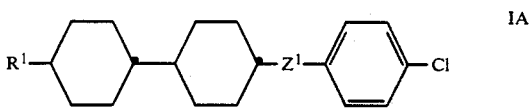

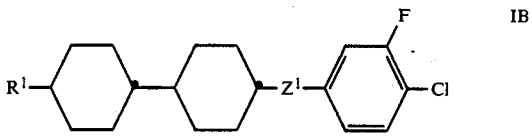

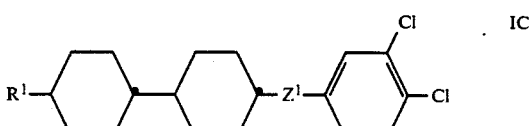

wherein $R^1$ and $Z^1$ have the above significances.

Preferred residues $R^1$ in the above formula are those with 2 to 7 carbon atoms, especially 2 to 5 carbon atoms. Vinyl and 1E-propenyl are especially preferred.

The compounds of formula I can be prepared in accordance with the invention by reacting an aldehyde of the formula

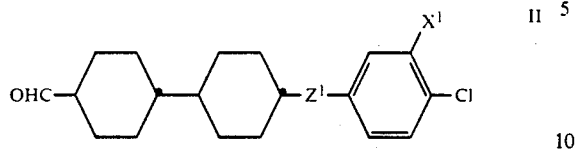

wherein $X^1$ and $Z^1$ have the above significances, with an alkyltriphenylphosphonium halide in the presence of a base.

The reaction with an alkyltriphenylphosphonium halide, (especially with an alkyltriphenylphosphonium chloride, bromide or iodide) in the presence of a base can be effected in a manner known per se. Potassium tert.-butylate, sodium methylate, sodium hydride, sodium amide and the like are suitable bases. The reaction is conveniently carried out in an inert organic solvent, for example an ether such as diethyl ether, tetrahydrofurna, dioxan or tert.butyl methyl ether. Temperature and pressure are not critical, but the reaction is generally carried out at atmospheric pressure and a temperature of room temperature to the reflux temperature.

When $R^1$ does not signify vinyl there are generally obtained E/Z mixtures which can be separated according to methods known per se, (for example, by chromatography on silica gel impregnated with silver nitrate). Further, if desired, the E/Z mixtures or the Z-isomers can be converted pre-dominantly into the E-form by equilibration with sulphinic acids, for example, benzenesulphinic acid or p-toluene-sulphinic acid.

The starting materials of formula II are known or are analogues of known compounds and can be prepared, for example, according to the methods described in the Examples.

The compounds of formula I can be used in the form of mixtures with one another and/or with other liquid crystal components such as for example, with substances from the classes of Schiff's based, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohextylcyclohexanes, phenylpyrimides, cyclohexylpyrimidines, phenyldioxanes, 2-cyclohexyl-1-phenylethanes, terphenyls, cyclohexylbiphenyls, cyclohexylphenylpyridimidines and the like. Such substances are known to the person skilled in the art and many of them are, moreover, commercially available.

The liquid crystalline mixture in accordance with the invention contain at least two components, of which at least one component is a compound of formula I. A second component and optionally further components can be additional compounds of formula I or other liquid crystal components. The compounds of formula I are especially suitable for nematic mixtures or, insofar as at least one component of the mixture is optically active, also for cholesteric mixtures.

Having regard to the good solubility of the compounds of formula I and having regard to their good miscibility with one another, their content in the mixtures in accordance with the invention can be relatively high. In general, however, a content of about 1–50 wt.%, especially about 5–30 wt.%, of compounds of formula I is preferred.

Preferably, the mixtures in accordance with the invention contain, in addition to one or more compounds of formula I, one or more compounds from the group of compounds of the formula

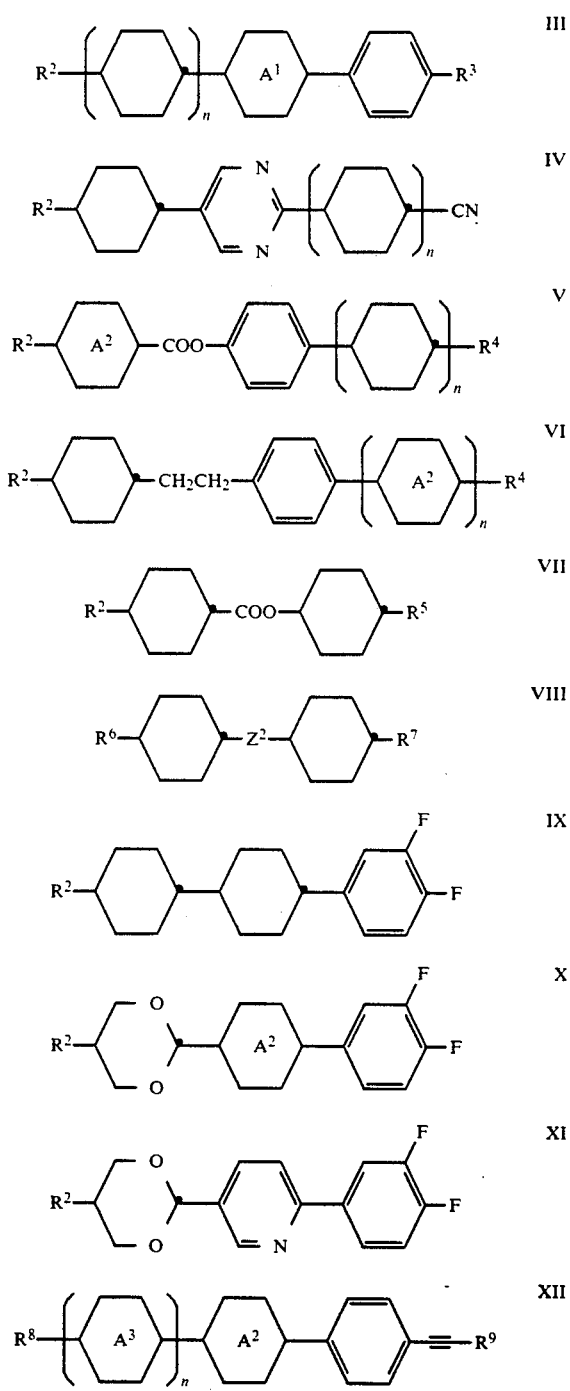

wherein n is the integer 0 or 1; $R^2$ and $R^5$ each individually are alkyl, 3E-alkenyl, 4-alkenyl or when positioned on a saturated ring also 1E-alkenyl; ring A1 is 1,4-phenylene, trans-1,4-cyclohexylene, pyrimidine-2,5-diyl or trans-1,3-dioxane-2,5-diyl; $R^3$ is cyano, —NCS, fluorine, alkyl, difluoromethoxy, trifluoromethoxy, 3E-alkenyl, 4-alkenyl, alkoxy, 2E-alkenyloxy or 3-alkenyloxy; ring $A^{2 \ l \ is}$ 1,4-phenylene or trans-1,4-cyclohexylene; $R^4$ is alkyl, 3E-alkenyl, 4-alkenyl or when positioned on a cyclohexane ring also 1E-alkenyl or when positioned on a benzene ring also cyano, —NCS, alkoxy, 2E-alkenyloxy or 3-alkenyloxy; $R^6$ is alkyl, 1E-alkenyl, 3E-alkenyl or 4-alkenyl; $Z^2$ is a single covalent bond or —$CH_2CH_2$—; $R^7$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl; $A^3$ is trans-1,4-cyclohexylene or trans-1,3-dioxane-2,5-diyl; $R^8$ is 3E-alkenyl, 4-alkenyl or, where n is the integer 1, $R^8$ also can be 1E-alkenyl; and $R^9$ is alkyl.

Unless otherwise stated, "alkyl" denotes a straight-chain alkyl group of 1 to 12 carbon atoms or a branched-chain alkyl group of 1 to 12 carbon atoms. Exemplary straight-chains alkyl groups are methyl, ethyl, propyl, butyl, pentyl, hexyl, heptyl octyl, nonyl, decyl, undecyl and dodecyl. Exemplary branched-chain alkyl groups are isopropyl, isobutyl, sec-butyl, 1-methylbutyl, 2-methylbutyl 3-methylpenyl, 4-methylhexyl and isopentyl. Lower alkyl denotes straight-chains and branched-chain alkyl groups of 1 to 5 carbon atoms.

The term "alkoxy" as well as any other groups in the specification containing "alkyl" denote moieties in which their "alkyl" portions are as defined previously.

The term "alkenyl" denotes straight-chain or branched alkenyl residues of 2–12 carbon atoms.

The term 4-alkenyl denotes alkenyl groups of 5–12 carbon atoms with the double bond positioned between the fourth and fifth carbon atoms, including either or both of the E and Z geometric isomers.

The term "saturated ring" above embraces trans-1,4-cyclohexylene and trans-1,3-dioxane-2,5-diyl. Residues $R^2$ to $R^7$ each preferably have a maximum of 12 carbon atoms, particularly a maximum of 7 carbon atoms. Straight-chain residues are generally preferred.

The manufacture of the liquid crystalline mixtures and of the electro-optical devices can be effected in a manner known per se.

The invention is illustrated in more detail by the following Examples. In the Examples C is a crystalline phase, N is a nematic phase and I is the isotropic phase. $V_{10}$ denotes the voltage for 10% transmission. $t_{on}$ and $t_{off}$ denote, respectively, the switching-on time and the switching-off time. $\Delta n$ denotes the optical anisotropy. Unless indicated otherwise (such as by other than the present tense verbs), the examples were carried out as written.

EXAMPLE 1 a) 4.53 mg of magnesium shavings and a granule of iodine were treated with 150 ml of tetrahydrofuran while stirring and gassing with nitrogen. Subsequently, the mixture was treated dropwise within 20 minutes with a solution of 38.4 g of 4-bromo-1-chlorobenzene in 150 ml of tetrahydrofuran and boiled at reflux for 1.25 hours. Thereafter, the reaction mixture was cooled to 0° C. and treated dropwise within 30 minutes at 0°–5° C. with a solution of 35.7 g of 8-(4-oxocyclohexyl)-1,4-dioxaspiro-[4.5]decane in 240 ml of tetrahydrofuran. The reaction mixture was stirred for a further 4 hours without cooling, then treated within 10 minutes with 240 ml of 10 percent ammonium chloride solution and extracted with diethyl ether. The ether phases were washed twice with water, dried over sodium sulfate, filtered and concentrated. There were thus obtained 54.7 g of 1-(4-chlorophenyl)-4-(1,4-dioxa-8-spiro[4,5]decyl)cyclohexanol as beige crystals.

b) A solution of 54.7 g of 1-(4-chlorophenyl)-4-(1,4-dioxa-8-spiro[4.5]decyl)cyclohexanol in 570 ml of ethylene chloride was treated with 6.95 ml of ethylene glycol and 6.95 g of Amberlyst* 15 (strongly acidic ion exchanger resin, Fluka AG) and refluxed for 2.3 hours through neutral aluminium oxide. Thereafter, the reaction mixture was cooled to room temperature, filtered and washed three times with water. The aqueous phases were extracted twice with methylene chloride. The organic phases were dried over sodium sulfate, filtered and concentrated. The crude product obtained (52.9 g) was dissolved in 150 ml of ethyl acetate. The solution was treated with active charcoal and filtered while warm. The filtrate was evaporated partially, then treated with methanol and stored at room temperature. There were thus obtained 24.9 g of 4-chloro-1-[4-(1,4-dioxo-8-spiro[4.5]-decyl)-1-cyclohexenyl]benzene as a colorless crystalline precipitate. Working-up of the mother liquor gave a further 6.3 g of product as colourless crystals.

c) A solution of 35.0 g of 4-chloro-1-[4-(1,4-dioxo-8-spiro[4.5]decyl)-1-cyclohexenyl]benzene in 1 l of toluene was treated with 2.6 g of palladium/charcoal (10%) and hydrogenerated at room temperature under normal pressure until the hydrogen uptake came to a standstill. Thereafter, the reaction mixture was filtered and the filtrate was concentrated, whereby 35.7 g of crude 4-chloro-1-[4-(1,4-dioxa-8-spiro[4.5]decyl)cyclohexyl]-benzene was obtained as a brownish oil. A suspension of 32.8 g of aluminium chloride in 215 ml of methylene chloride was treated at $-18°$ C. while stirring and gassing with nitrogen within 10 minutes with a solution of the hydrogenation product (35.7 g of brownish oil) in 110 ml of methylene chloride and the mixture was stirred at 0° C. for a further 30 minutes. Subsequently, the reaction mixture was poured on to 600 ml of ice/water, stirred for 10 minutes and then extracted three times with methylene chloride. The organic phases were washed in succession with water, with saturated sodium hydrogen carbonate solution and a further twice with water, then dried over sodium sulfate, filtered and concentrated. There were thus obtained 31.1 g of 4-chloro-1[trans-4-(1,4-dioxa-8-spiro[4,5-]decyl)-cyclohexyl]benzene as beige crystals.

d) A mixture of 31.1 g of 4-chloro-1-[trans-4-(1,4-dioxa-8-spiro[4.5]decyl)cyclohexyl]benzene, 207 ml of toluene and 103 ml of formic acid was stirred at room temperature while gassing with nitrogen for 1.25 minutes. Thereafter, the reaction mixture was poured into 500 ml of water and extracted three times with methylene chloride. The organic phases were washed once with saturated sodium hydrogen carbonate solution and twice with water, dried over sodium sulfate, filtered and concentrated. There were thus obtained 30.3 g of trans-4'-(4-chlorophenyl)-[1,1'-bicyclohexyl]-4-one as beige crystals.

e) A suspension of 35.5 g of methoxymethyl-triphenylphosphonium chloride in 210 ml of tert.butyl methyl ether was treated at $-15°$ C. while stirring and gassing with nitrogen with 12.2 g of potassium tert-butylate. The suspension was stirred at 5° C. for a further 30 minutes, then treated dropwise at 0°–5° C. within 40 minutes with a solution of 20 g of trans-4'-(4-chlorophenyl)-[1,1'-bicyclohexyl]-4-one in 50 ml of tetrahydrofuran and 200 ml of tert.butyl methyl ether and stirred at room temperature for a further 1 hour. Subsequently, the reaction mixture was suction filtered and the filtrate was concentrated. The crude product obtained (45.0 g) was treated with 250 ml of hexane. The mixture was stirred at room temperature for 10 minutes and suction filtered. Concentration of the filtrate gave 27.0 g of crude product as a red-brownish oil. Purification of this product by chromatography on silica gel with hexane and hexane/ethyl acetate finally yielded 18.1 g of trans-4-(4-chlorophenyl)-4'-(methoxymethylidene)-[1,1'-bicyclohexyl] as colourless crystal.

f) A solution of 18.1 g of trans-4-(4-chlorophenyl)-4'-(methoxymethylidene)-[1,1'-bicyclohexyl] in 90 ml of tetrahydrofuran was treated with 22.5 ml of 2N hydrochloric acid and boiled at reflux for 30 minutes while stirring and gassing with nitrogen. Subsequently, the reaction mixture was cooled to room temperature, powered into 400 ml of water and extracted three times with methylene chloride. The organic phases were washed twice with water, dried over sodium sulfate, filtered and concentrated. The residue (17.0 g) was dissolved in 150 ml of tert.butyl methyl ether. The solution was evaporated to a large extent and then treated with 200 ml of methanol. Crystallization at $-25°$ C. gave 7.5 g of product as a colourless, crystalline precipitate. Working-up of the mother liquor yielded a further 8.5 g of product. Recrystallization of the product obtained finally gave 13.6 g of trans-4'-(4-chlorophenyl)-[1,1'-bicycohexyl]-trans-4-carboxal-dehyde as colourless crystals.

g) A suspension of 2.0 g of ethyltriphenylphosphonium bromide in 275 ml of tert.butyl methyl ether was treated with 6.75 g of potassium tert.butylate while stirring and gassing with nitrogen and stirred at room temperature for a further 1 hour. Subsequently, the suspension was treated dropwise with a solution of 10.0 g of trans-4'-(4-chlorophenyl)-[1,1'-bicyclohexyl]-trans-4-carboxaldehyde in 40 ml of tetrahydrofuran and 100 ml of tert.butyl methyl ether and stirred for a further 45 minutes while cooling with an ice bath. Thereafter, the reaction mixture was suction filtered and the filtrate was concentrated in a vacuum. The beige, crystalline residue (21.7 g) was treated with 250 ml of hexane. The mixture was stirred for 10 minutes and then suction filtered. Concentration of the filtrate in a vacuum gave 11.6 g of crude product as beige crystals. Purification by chromatography on silica gel yielded 9.5 g of 1-[trans-4-(trans-4-(1-propenyl)cyclohexyl)cyclohexyl]-4-chlorobenzene with an E/Z ratio of 11:88 as colourless crystals.

h) A solution of 9.5 g of 1-trans-4-(trans-4-(1-propenyl)-cyclohexyl)cyclohexyl]-4-chlorobenzene in 115 ml of toluene was treated at room temperature while stirring and gassing with nitrogen with 9.4 ml of 2N hydrochloric acid and 1.43 g of sodium benzenesulfinate and heated (oil bath temperature 60°-65° C.) for 2.25 hours. Thereafter, the reaction mixture was cooled to room temperature, poured into 150 ml of 10 percent sodium hydrogen carbonate solution and extracted three times with diethyl ether. The organic phases were washed twice with water, dried over sodium sulfate, filtered and concentrated. Recrystallization of the crude product obtained (9.7 g) from tert.butyl methyl ether/isopropanol gave 7.6 g of 1-[trans-4-(trans-4-(1E-propenyl)cyclohexyl)-cyclohexyl]-4-chlorobenzene as colorless crystals; m.p. (C-N) 106.9° C. cl.p. (N-I) 228.5° C.

The following compounds can be prepared in an analogous manner:

1-[trans-4-(trans-4-Vinylcyclohexyl)cyclohexyl]-4-chlorobenzene, m.p. (C-N) 102.4° C., cl.p. (N-I) 179.5° C.;

1-[trans-4-(trans-4-(1E-pentenyl)cyclohexyl)cyclohexyl]-4-chlorobenzene, m.p. (C-N) 89.4° C., cl.p. (N-I) 207.1° C.;

1-[trans-4-(trans-4-vinylcyclohexyl)cyclohexyl]-3-fluoro-4-chlorobenzene, m.p. (C-N) 83.5° C., cl.p. (N-I) 145° C.;

1-[trans-4-(trans-4-(1E-propenyl)cyclohexyl)cyclohexyl]-3-fluoro-4-chlorobenzene, m.p. (C-N) 90.8° C., cl.p. (N-I) 195° C.;

1-[trans-4-(trans-4-(1E-pentenyl)cyclohexyl)cyclohexyl-3-fluoro-4-chlorobenzene, m.p. (C-N) 64.8° C., cl.p. (N-I) 173.5° C.;

1-[trans-4-(trans-4-vinylcyclohexyl)cyclohexyl]-3,4-dichlorobenzene, m.p. (C-N) 64.3° C.; cl.p. (N-I) 79° C.;

1-[trans-4-(trans-4-(1E-propenyl)cyclohexyl)cyclohexyl)-3,4-dichlorobenzene, m.p. (C-N) 76.3° C.; cl.p. (N-I) 126.5° C.;

1-[trans-4-(trans-4-(1E-pentenyl)cyclohexyl)cyclohexyl]-3,4-dichlorobenzene, m.p. (C-N) 52.6° C., cl.p. (N-I) 113.4° C.

EXAMPLE 2 a) A suspension of 133.3 g of aluminium chloride in 250 ml of methylene chloride was treated dropwise at 20° C. while cooling and gassing with nitrogen with a solution of 174.2 g of 4-phenylcyclohexanone in 250 ml of methylene chloride. The reaction mixture was stirred for a further 30 minutes until a clear solution was obtained. In the meanwhile, a suspension of 133.3 g of aluminium chloride in 500 ml of methylene chloride was treated with 172 ml of oxalyl chloride while gassing with nitrogen. This mixture was subsequently treated dropwise at 20°-25° C. within 1 hour with the above solution of the 4-phenylcyclohexanone-aluminium chloride complex. The reaction mixture was stirred for a further 30 minutes, then cooled to 2° C. and added dropwise within 20 minutes while stirring to a solution of 300 g of calcium chloride in 1 l of water. The mixture was stirred at room temperature for a further 1.5 hours and then poured on to 500 ml of ice/water. The organic phase was separated and washed with 500 ml of semi-saturated sodium chloride solution. The aqueous phases were back-extracted twice with 500 ml of methylene chloride each time. The combined organic phase was dried over sodium sulfate, filtered and concentrated. The oily 4-(4-oxocyclohexyl)benzoyl chloride obtained was dissolved in 400 ml of toluene and this solution was added dropwise to a mixture of 150 ml of methanol, 200 ml of pyridine and 1 l of toluene. The reaction mixture was left to stand overnight and then washed in succession with water, 3N hydrochloric acid, semi-saturated sodium hydrogen carbonate solution and again with water, dried over sodium sulfate, filtered and concentrated. Recrystallization of the residue from toluene at $-25°$ C. gave 128 g of pure methyl 4-(4-oxocyclohexyl)-benzoate with m.p. 91°-92° C.

b) A suspension of 236 g of dry methoxymethyl-triphenylphosphonium chloride in 900 ml of tetrahydrofuran was treated with 77 g of potassium tert.butylate while gassing with nitrogen. The suspension was stirred for a further 30 minutes, then cooled to 0° C. and treated dropwise within 30 minutes with a solution of 128 g of methyl 4-(4-oxo-cyclohexyl)benzoate in 420 ml of tetrahydrofuran. The reaction mixture was stirred at 0° C. for a further 3 hours, then treated with 550 ml of saturated sodium hydrogen carbonate solution and extracted three times with diethyl ether. The organic phases were washed with water, dried over sodium sulfate, filtered and concentrated. The residue was dissolved in 2.5 l of hexane and 0.8 l of methanol/water (vol. 4:1). The hexane phase was washed with 300 ml of methanol/water (vol. 4:1), dried over sodium sulfate, filtered and concentrated. There were thus obtained 123 g of methyl 4-[4-(methoxymethylidene)-cyclohexyl benzoate with m.p. 58° C.

c) A mixture of 123 g of methyl 4-[4-(methoxymethylidene)-cyclohexyl]benzoate, 1 l of toluene and 500 ml of formic acid was stirred vigorously at room temperature overnight. The formic acid phase was separated. The toluene phase was washed neutral with water, dried over sodium sulfate, filtered and concentrated. The crude cis/trans mixture obtained was dissolved in 600 ml of methanol. The solution was added dropwise while gassing with nitrogen at 3° C. within 10 minutes to 1.2 l of a 0.1N methanolic potassium hydroxide solution. The reaction mixture was stirred at 3° C. for a further 1 hour, then poured on to ice/water and extracted with diethyl ether. The organic phases were washed neutral with water, dried over sodium sulfate, filtered and concentrated. Recrystallization of the residue from tert.butyl methyl ether gave 88.5 g of methyl 4-(trans-4-formylcyclohexyl)-benzoate with m.p. 84°–85° C.

d) A solution of 88.5 g of methyl 4-trans-4-formylcyclohexyl)benzoate in 700 ml of toluene and 25 ml of diethylene glycol was treated with 1.5 ml of 10 percent (v/V) sulfuric acid while stirring and heated to boiling for 1 hour, whereby moist toluene was distilled off and replaced by the addition of fresh toluene. Subsequently, the reaction solution was treated with 1 ml of triethylamine. The mixture was washed three times with 150 ml of water each time, dried over sodium sulfate, filtered and concentrated. Twofold recrystallization of the residue from tert.butyl methyl ether at −25° C. gave 75.4 g of pure methyl 4-[trans-4-(1,3-dioxolan-2-yl)cyclohexyl]benzoate with m.p. 110°–111° C.

e) A mixture of 100 g of methyl 4-[trans-4-(1,3-dioxolan-2-yl)cyclohexyl]benzoate, 10 g of 5% rhodium/aluminium oxide, 1 l of methanol and 1 ml of triethylamine was hydrogenated at 60° C. under 10 bar of hydrogen until the hydrogen uptake came to a standstill. The mixture was filtered and the filtrate was concentrated. There were thus obtained 97 g of methyl trans-4-( 1,3-dioxolan-2-yl)-[1,1'-bicyclohexyl]-4-carboxylate (cis/trans ratio 60:40) which were treated with 19.3 g of methanol and 3.4 ml of 10 percent sodium hydroxide solution. The solvent was distilled off while stirring and gassing with nitrogen until a boiling point of 90° C. was achieved. Subsequently, the mixture was stirred at this temperature for a further 1.5 hours. The semi-solid mixture obtained was cooled slowly and at the same time treated cautiously with 300 ml of methylene chloride. Subsequently, the mixture was washed with 150 ml of saturated sodium hydrogen carbonate solution, dried over sodium sulfate, filtered and concentrated. Recrystallization of the residue from 800 ml of hexane gave 80.7 g of pure methyl 4'-(1,3-dioxolan-2-yl)-[1,1'-bicyclohexyl]-trans-4-carboxylate with m.p. 126°–127° C.

f) A suspension of 3.4 g of lithium aluminium hydride in 200 ml of absolute diethyl ether was treated dropwise within 2 hours with a solution of 26.7 g of methyl 4'-(1,3-dioxolan-2-yl)-[1,1'-bicyclohexyl]-trans-4-carboxylate in 500 ml of absolute diethyl ether. The reaction mixture was stirred for a further 2 hours and poured cautiously on to 25 ml of ice/water and 60 ml of 25 percent hydrochloric acid. The aqueous phase was separated and extracted with diethyl ether. The combined organic phases were washed neutral with water, dried over sodium sulfate, filtered and concentrated. There were thus obtained 23.7 g of trans-4'-(1,3-dioxolan-2-yl)-[1,1'-bicyclohexyl]-trans-4-carbinol.

g) A suspension of 34.5 g of pyridinium chlorochromate in 150 ml of methylene chloride was treated dropwise within 30 minutes with a solution of 23.7 g of trans-4'-(1,3-dioxolan-2-yl)-[ 1,1'-bicyclohexyl]-trans-4-carbinol. The reaction mixture was stirred at room temperature for a further 3 hours, then poured into 500 ml of absolute diethyl ether and decanted off from the residue. The residue was washed a further three times with 100 ml of diethyl ether each time. Filtration and concentration of the solution gave 19.8 g of trans-4'-(1,3-dioxolan-2-yl)-[1,1'-bicyclohexyl]-trans-4-carboxyaldehyde.

h) A solution of 29.4 g of triphenylphosphine in 200 ml of toluene is treated dropwise with 20.5 g of 4-chlorobenzyl bromide. The mixture is heated to 65° C. for 3 hours and then to boiling for 2 hours. After cooling to room temperature the precipitate is removed by filtration, washed with toluene and dried in a vacuum. The 4-chlorobenzyl-tri-phenylphosphonium bromide obtained is suspended in 500 ml of diethyl ether. The suspension is treated with 9.5 g of potassium tert.butylate while gassing with nitrogen, stirred at room temperature for a further 30 minutes and then treated dropwise at 20° C. with a solution of 19.8 g of trans-4'-(1,3-dioxolan-2-yl)-[1,1'-bicyclohexyl]-trans-4-carboxaldehyde in 250 ml of absolute diethyl ether. The reaction mixture is stirred at room temperature for a further 2.5 hours. Subsequently, the mixture is washed with 500 ml of semi-saturated sodium hydrogen carbonate solutions and with 300 ml of water, dried over sodium sulfate, fitted and concentrated. The residue is dissolved in 200 ml of hexane and 120 ml of methanol/water (vol. 4:1). The hexane phase is separated, washed with 40 ml of methanol/water (vol. 4:1), dried over sodium sulfate, filtered and concentrated. Purification of the residue by chromatography on silica gel with hexane/ethyl acetate (vol. 9:1) gives trans-4-(1,3-dioxolan-2-yl)-trans-4'-(4-chlorostyryl)-[1,1'-bicyclohexyl].

i) A solution of 23.6 g of trans-4-(1,3-dioxolan-2-yl)-trans-4'-(4-chlorostyryl)-[1,1'-bicyclohexyl] in 1.2 l of dioxan and 2.5 ml of triethylamine is hydrogenated at room temperature and under normal pressure with 2.5 g of 5% palladium/charcoal until the hydrogen uptake comes to a standstill. Filtration of the reaction mixture and concentration of the filtrate gives trans-4-(1,3-dioxolan-2-yl)-trans-4'-(4-chlorophen-ethyl)-[1,1'-bicyclohexyl].

j) A mixture of 12.3 g of trans-4-(1,3-dioxolan-2-yl)-trans-4'-(4-chlorophenethyl)-[1,1'-bicyclohexyl], 300 ml of toluene and 50 ml of formic acid is stirred overnight under a nitrogen atmosphere. Subsequently, the formic acid phase is separated. The toluene phase is washed with water and with saturated sodium hydrogen carbonate solution, dried over sodium sulfate, filtered and concentrated. The trans-4'-(4-chlorophenethyl)-[1,1'-bicyclohexyl]-trans-4-carboxaldehyde obtained is recrystallized from methanol.

k) In an analogous manner to Example 1g) and 1h), trans-4'-(4-chlorophenethyl)-[1,1'-bicyclohexyl]-trans-4-carboxaldehyde is converted into 1-[2-[trans-4-(trans-4-(1E-propenyl)cyclohexyl)-cyclohexyl]ethyl]-4-chlorobenzene, m.p. (C-N) 81.4° C., cl.p. (N-I) 186° C.

The following compounds can be prepared in an analogous manner:

1-[2-[trans-4-(trans-4-vinylcyclohexyl)cyclohexyl]ethyl]-4-chlorobenzene; m.p. (C-N) 62.6° C., cl.p. (N-I) 147° C.;

1-[2-[trans-4-(trans-4-vinylcyclohexyl)cyclohexyl]ethyl]-3-fluoro-4chlorobenzene, m.p. (C-N) 49.4° C., cl.p. (N-I) 127.5° C.;

1-[2-[trans-4-(trans-4-(1E-propenyl)cyclohexyl)cyclohexyl]ethyl]-3-fluoro-4-chlorobenzene, m.p. (C-N) 72° C.; cl.p. (N-I) 165° C.;

1-[2-trans-4-(trans-4-vinylcyclohexyl)cyclohexyl]ethyl-3,4-dichlorobenzene;

1-[2-[trans-4-(trans-4-(1E-propenyl)cyclhexyl)cyclohexyl]ethyl]-3,4-dichlorobenzene.

EXAMPLE 3

Binary mixtures (BM) with 4-trans-4-pentylcyclohexyl)benzonitrile were prepared in order to investigate the properties of the compounds of formula I. The threshold potential and the response times were measured at 22° C. in a TN cell (low bias tilt) having a plate separation of 8 mm; with the 2.5-fold value of the threshold potential being chosen as the operating voltage. The corresponding data for pure 4-trans-4-pentylcyclohexyl)benzonitrile were: cl.p. (N-I) 54.6° C. $V_{10}=1.62$ V, $t_{on}=30$ ms, $t_{off}=42$ ms, $\Delta n=0.120$.

BM-1
90 wt.% of 4-(trans-4-pentylcylcohexyl)benzonitrile,
10 wt.% of 1-[trans-4-vinylcyclohexyl)cyclohexyl]-4-chlorobenzene;
cl.p. (N-I) 63.5° C., $V_{10}=1.65$ V, $t_{on}=26$ ms, $t_{off}=40$ ms, $\Delta n=0.125$.

BM-2
80 wt.% of 4-(trans-4-pentylcyclohexyl)benzonitrile,
20 wt.% of 1-[trans-4-(trans-4-vinylcyclohexyl)cyclohexyl]-4-chlorobenzene;
cl.p. (N-I) 73.8° C., $V_{10}=1.69$ V, $t_{on}=24$ ms, $t_{off}=39$ ms, $\Delta n=0.126$.

BM-3
90 wt.% of 4-(trans-4-pentylcyclohexyl)benzonitrile,
10 wt.% of 1-[trans-4-(trans-4-(1E-propenyl)cyclohexylcyclohexyl]-4-chlorobenzene;
cl.p. (N-I) 66.1° C., $V_{10}=1.66$ V, $t_{on}=27$ ms, $t_{off}=36$ ms, $\Delta n=0.127$.

BM-4
λwt.% of 4-(trans-4-pentylcyclohexyl)benzonitrile,
20 wt.% of 1-[trans-4-(trans-4-(1E-propenyl)cyclohexyl)-cyclohexyl]-4-chlorobenzene;
cl.p. (N-I) 78.4° C., $V_{10}=1.84$ V, $t_{on}=21$ ms, $t_{off}=36$ ms, $\Delta n=0.123$.

BM-5
90 wt.% of 4-trans-4-pentylcyclohexyl)benzonitrile,
10 wt.% of 1-[trans-4-(trans-4-(1E-pentenyl)cyclohexyl)-cyclohexyl]-4-chlorobenzene;
cl.p. (N-I) 64.5° C., $V_{10}=1.64$ V, $t_{on}=29$ ms, $t_{off}=40$ ms, $\Delta n=0.124$.

BM-6
80 wt.% of 4-(trans-4-pentylcyclohexyl)benzonitrile,
20 wt.% of 1-[trans-4-(trans-4-(1E-pentenyl)cyclohexyl)-cyclohexyl]-4-chlorobenzene;
cl.p. (N-I) 75.3° C., $V_{10}=1.89$ V, $t_{on}=24$ ms, $t_{off}=40$ ms, $\Delta n=0.125$.

BM-7
90 wt.% of 4-(trans-4-pentylcylcohexyl)benzonitrile,
10 wt.% of 1-[trans-4-(trans-4-vinylcyclohexyl)cyclohexyl]-3-fluoro-4-chlorobenzene;
cl.p. (N-I) 59.5° C., $V_{10}=1.58$ V, $t_{on}=23$ ms, $t_{off}=40$ ms, $\Delta n=0.123$.

BM-8
80 wt.% of 4-(trans-4-pentylcyclohexyl)benzonitrile,
20 wt.% of 1-[trans-4-(trans-4-vinylcyclohexyl)cyclohexyl]-3-fluoro-4-chlorobenzene;
cl.p. (N-I) 66.3° C., $V_{10}=1.62$ V, $t_{on}=25$ ms, $t_{off}=40$ ms, $\Delta n=0.125$.

BM-9
90 wt.% of 4-(trans-4-pentylcyclohexyl)benzonitrile.
10 wt.% of 1-[trans-4-(trans-4-(1E-propenyl)cyclohexyl)-cyclohexyl-3-fluoro-4-chlorobenzene; cl.p. (N-I) 62.7° C., $V_{10}=1.61$V, $t_{on}=24$ ms, $t_{off}=39$ ms, $\Delta n=0.125$.

BM-10
90 wt.% of 4-(trans-4-pentylcyclohexyl)benzonitrile,
10 wt.% of 1-trans-4-(trans-4-(1E-pentenyl)cyclohexyl)-cyclohexyl]-3-fluoro-4-chlorobenzene;
cl.p. (N-I) 62.0° C., $V_{10}=1.60$ V, $t_{on}=23$ ms, $t_{off}=39$ ms, $\Delta n=0.123$.

BM-11
90 wt.% of 4-(trans-4-pentylcyclohexyl)benzonitrile,
10 wt.% of 1-[trans-4-(trans-4-vinylcyclohexyl)cyclohexyl]-3,4-dichlorobenzene;
cl.p. (N-I) 55.2° C., $V_{10}=1.49$ V, $t_{on}=27$ ms, $t_{off}=44$ ms, $\Delta n=0.121$.

BM-12
90 wt.% of 4-(trans-4-pentylcylcohexyl)benzonitrile,
10 wt.% of 1-trans-4-(1E-propenyl)cyclohexyl)cyclohexyl]-3,4-dichlorobenzene;
cl.p. (N-I) 58.5° C., $V_{10}=1.55$ V, $t_{on}=27$ ms, $t_{off}=47$ ms, $\Delta n=0.122$.

BM-13
90 wt.% of 4-(trans-4-pentylcyclohexyl)benzonitrile,
10 wt.% of 1-[2-[trans-4-(trans-4-vinylcyclohexyl)cyclohexyl]ethyl]-4-chlorobenzene,
cl.p. (N-I) 61° C., $V_{10}=1.75$ V, $t_{on}=23$ ms, $t_{off}=39$ ms, $\Delta n=0.124$.

BM-14
80 wt.% of 4-(trans-4-pentylcyclohexyl)benzonitrile,
20 wt.% of 1-[2-[trans-4-(trans-4-vinylcyclohexyl)cyclohexyl]ethyl]-4-chlorobenzene,
cl.p. (N-I) 69.9° C., $V_{10}=1.89$ V, $t_{on}=23$ ms, $t_{off}=36$ ms, $\Delta n=0.125$.

BM-15
90 wt.% of 4-(trans-4-pentylcyclohexyl)benzonitrile,
10 wt.% of 1-[2-[trans-4-(trans-4-(1E-propenyl)cyclohexyl)cyclohexyl]ethyl]-4-chlorobenzene,
c.p. (N-I) 64.2° C., $V_{10}=1.74$ V, $t_{on}=25$ ms, $t_{off}=40$ ms, $\Delta n=\mathbf{0.126}$.

BM-16
80 wt.% of 4-(trans-4-pentylcylcohexyl)benzonitrile, 20 wt.% of 1-[2-[trans-4-(trans-4-(1E-propenyl)cyclohexyl)cyclohexyl]ethyl]-4-chlorobenzene.
cl.p. (N-I) 71.1° C., $V_{10}=1.93$ V, $t_{on}=23$ ms, $t_{off}=37$ ms, $\Delta n=0.128$.

We claim:

1. A compound of the formula (I)

wherein $Z^1$ is a single covalent bond or —CH$_2$CH$_2$—, $X^1$ is hydrogen, fluorine or chlorine, and $R^1$ is 1E-alkenyl with 2 to 12 carbon atoms.

2. A compound according to claim 1, wherein $R^1$ is a straight-chain residue.

3. A compound according to claim 1, wherein $R^1$ has 2–7 carbon atoms.

4. A compound according to claim 3, wherein $R^1$ has 2–5 carbon atoms.

5. A compound to claim 1, wherein $R^1$ is 1E-propenyl and $X^1$ is hydrogen.

6. A liquid crystalline mixture having at least 2 components, wherein at least one component is a compound of the formula:

(I)

wherein $Z^1$ is a single covalent bond or —CH$_2$CH$_2$—, $X^1$ is hydrogen, fluorine or chlorine, and $R^1$ is 1E-alkenyl with 2 to 12 carbon atoms.

7. A liquid crystalline mixture according to claim 6, wherein the compound of formula I amounts to about 1 to about 50 wt% of the mixture.

8. A liquid crystalline mixture according to claim 6, wherein the compound of formula I amounts to about 1 to about 30 wt% of the mixture.

9. A liquid crystalline mixture according to claim 6, which includes at least one compound of formula I and at least one compound selected from the group of compounds of the formulas

III

IV

V

VI

VII

VIII

IX

X

XI and

XII wherein n is the integer 0 or 1; $R^2$ and $R^5$ each individually are alkyl, 3E-alkenyl, 4-alkenyl or when positioned on a saturated ring also 1E-alkenyl; ring $A^1$ is 1,4-phenylene, trans-1,4-cyclohexylene, pyrimidine-2,5-diyl or trans-1,3-dioxane-2,5-diyl; $R^3$ is cyano, —NCS, fluorine, alkyl, difluoromethoxy, trifluoro-methoxy, 3E-alkenyl, 4-alkenyl, alkoxy, 2E-alkenyloxy or 3-alkenyloxy; ring $A^2$ is 1,4-phenylene or trans-1,4-cyclohexylene; $R^4$ is alkyl, 3E-alkenyl, 4-alkenyl or when positioned on a cyclohexane ring also 1E-alkenyl or when positioned on a benzene ring also cyano, —NCS, alkoxy, 2E-alkenyloxy or 3-alkenyl- oxy; $R^6$ is alkyl, 1E-alkenyl, 3E-alkenyl or 4-alkenyl; $Z^2$ is a single covalent bond or —CH$_2$CH$_2$—; $R^7$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl; $A^3$ is trans-1,4-cyclohexylene or trans-1,3-dioxane-2,5-diyl; $R^8$ is 3H-alkenyl, 4-alkenyl or, where n is the integer 1, $R^8$ also can be 1E-alkenyl; and $R^9$ is alkyl.

10. An electro-optical cell comprising:
(a) two plate means;
(b) liquid crystal means disposed between the two plate means and including a compound of the formula:

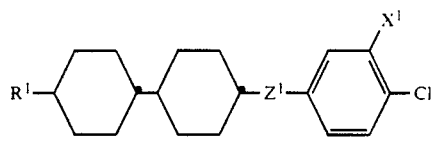

wherein $Z^1$ is a single covalent bond or —$CH_2CH_2$—, $X^1$ is hydrogen, fluorine or chlorine, and $R^1$ is 1E-alkenyl with 2 to 12 carbon atoms; and
(c) means for applying electric potential to said plate means.

* * * * *

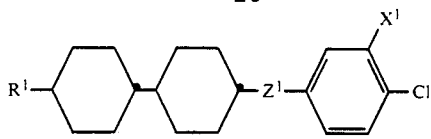

wherein $Z^1$ is a single covalent bond or —$CH_2CH_2$—, $X^1$ is hydrogen, fluorine or chlorine, and $R^1$ is 1E-alkenyl with 2 to 12 carbon atoms; and
(c) means for applying electric potential to said plate means.

* * * * *